United States Patent [19]

Merwin et al.

[11] Patent Number: 4,676,796
[45] Date of Patent: Jun. 30, 1987

[54] MIDDLE EAR PROSTHESIS

[75] Inventors: Gerald E. Merwin; Derek B. Spilman; Larry L. Hench, all of Gainesville, Fla.

[73] Assignee: University of Florida, Gainesville, Fla.

[21] Appl. No.: 737,426

[22] Filed: May 24, 1985

[51] Int. Cl.⁴ .............................................. A61F 2/18
[52] U.S. Cl. ..................................................... 623/10
[58] Field of Search ............................. 623/10, 66, 16; 128/1 R

[56] References Cited

U.S. PATENT DOCUMENTS 3,473,170  10/1969  Haase et al. ........................... 623/10
3,711,869  1/1973   Shea, Jr. ................................. 623/10
4,281,419  8/1981   Treace ................................... 623/16
4,437,192  3/1984   Fujiu et al. ............................ 623/16

Primary Examiner—Richard J. Apley
Assistant Examiner—Alan W. Cannon
Attorney, Agent, or Firm—Dennis P. Clarke

[57] ABSTRACT

A middle ear prosthesis is constructed of a bio-active bio-compatible glass. The prosthesis includes a substantially disc-like base member, one base surface of which is adapted to bond to the tympanic membrane, and a substantially cylindrical stem member projecting from the other base surface. The axis of the stem member is offset from the center of the base member and perpendicular to the base surface.

2 Claims, 12 Drawing Figures

MIDDLE EAR PROSTHESIS

BACKGROUND OF INVENTION

RELATED APPLICATION

The invention described herein is related to that described in U.S. patent application Ser. No. 486,421, filed Apr. 19, 1983.

FIELD OF INVENTION

The present invention relates to a novel middle ear prosthesis.

PRIOR ART

Middle ear prostheses constructed of certain bio-active, bio-compatible glasses are described in U.S. application Ser. No. 486,421, filed Apr. 19, 1983, the entire disclosure of which is incorporated herein by reference.

SUMMARY OF THE INVENTION

The present invention comprises middle ear prostheses constructed of the above-described bio-active glasses having specific shapes and designs especially adapted to meet specific surgical needs in the reconstruction of all or part of the ossicular chain. One embodiment of the invention comprises a middle ear prosthesis comprising a substantially disc-like base member, one base surface of which is especially adapted to interface with and bond to the thin collagen layer of the tympanic membrane or grafted tympanic membrane of the middle ear and an integral substantially cylindrical stem member projecting outwardly from the other base surface of the base member, the stem member having a smaller diameter than the base member and the axis of the stem member being off-set with respect to the center of and substantially perpendicular to the base surface of the base member.

Another embodiment of the invention comprises a middle ear prosthesis comprising a substantially disc-like base member, one base surface of which is especially adapted to interface with and bond to the thin collagen layer of the tympanic membrane or grafted tympanic membrane of the middle ear and an integral substantially cylindrical stem member projecting outwardly from the other base surface of the base member, the stem member having a smaller diameter than the base member and the axis of the stem member being off-set with respect to the center of and substantially non-perpendicular to the base surface of the base member.

An additional embodiment of the invention comprises a middle ear prosthesis comprising a base member having two opposed flat surfaces, one of the flat surfaces being especially adapted to interface with and bond to a malleus handle of the middle ear and an integral substantially cylindrical stem member projecting outwardly from the other of the flat surfaces of the base member, the stem member having a smaller cross-section than the base member and the axis of the stem member being off-set with respect to the center of and substantially perpendicular to the base surface of the base member.

A further embodiment of the invention comprises a middle ear prosthesis comprising a base member having two opposed flat surfaces, one of the flat surfaces being especially adapted to interface with and bond to a malleus handle of the middle ear and an integral substantially cylindrical stem member projecting outwardly from the other of the flat surfaces of the base member, the stem member having a smaller cross-section than the base member and the axis of the stem member being off-set with respect to the center of and substantially non-perpendicular to the base surface of the base member.

DETAILED DESCRIPTION OF THE INVENTION

In the preferred embodiments of the invention, the end of stem member proximal to the base member is flared toward the base surface thereof.

Figure 1B:
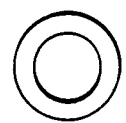
FIGS. 1b, 2b, 3b and 4b are bottom plan views of various embodiments of the Middle Ear Prosthesis.
Figure 1A:
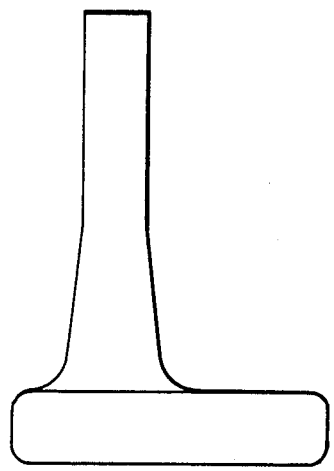
FIGS. 1a, 2a, 3a and 4a are side elevational views of various embodiments of the Middle Ear Prosthesis, it being understood that the other sides correspond as in mirror images.
Figure 1:
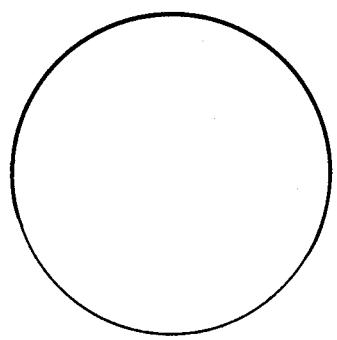
FIGS. 1, 2, 3 and 4 are top plan views of various embodiments of the Middle Ear Prosthesis.
Figure 2B:
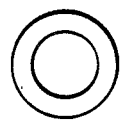
Figure 2A:
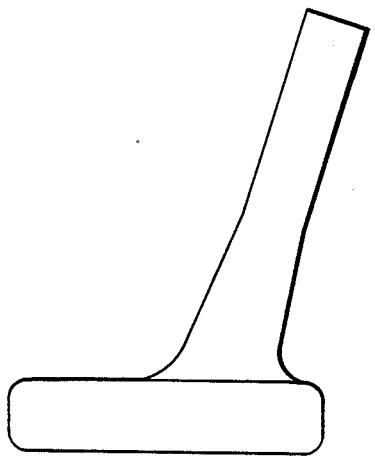
Figure 2:
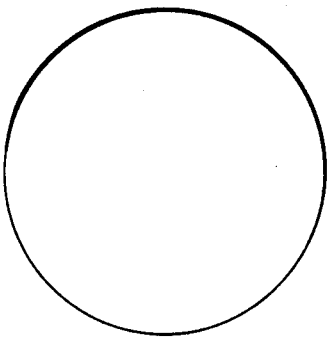

The middle ear prosthesis may take four different forms or shapes, each of which is specifically created to meet a specific anticipated surgical need. Two types of device (FIGS. 1 and 2) have circular cross-section bases which are designed to interface with and bond to the thin collagen layer of the tympanic membrane or grafted tympanic membrane. The stem of the device, which is an integral part of the component, is designed to bridge the space of the middle ear and bond through a bio-active bond to the stapes footplate, stapes superstructures, incus or grafted membrane of the oval window.

The straight stem design (FIGS. 1, 1a and 1b) is specifically for the surgical situation where no malleus handle and no stapes superstructure are present and the prosthesis stem must traverse the narrow oval window niche, but where the facial ridge is sufficiently high that the tympanic membrane or tympanic membrane graft is parallel to the stapes footplate or oval window graft membrane.

The angled stem (FIGS. 2, 2a and 2b) is designed for the surgical situation where no stapes superstructure is present and the prosthesis stem must traverse the narrow oval window niche but where the facial ridge is sufficiently low that the tympanic membrane or tympanic membrane graft is angulated laterally from posterior to anterior, relative to the stapes footplate or oval window graft membrane.

Figure 3B:
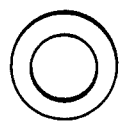
Figure 3A:
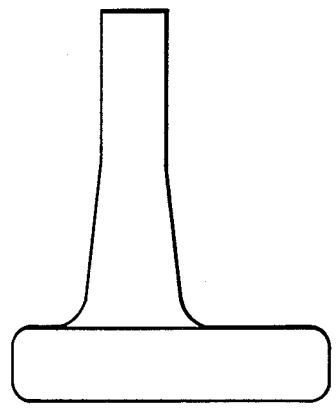
Figure 3:
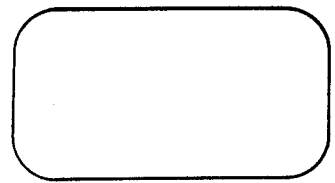
Figure 4:
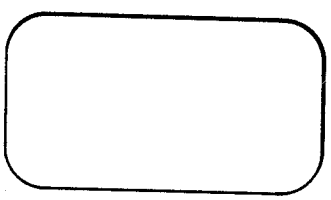

Two devices (FIGS. 3 and 4) have generally rectangular bases which are designed to fit in contact with a malleus handle when the handle is present and to bond to the malleus handle and tympanic membrane or tympanic membrane graft.

The straight stem design (FIGS. 3, 3a and 3b) is specifically for the surgical situation where the measured distance from head of stapes to malleus handle is within 0.1 inch in the anterior to posterior dimension.

Figure 4A:
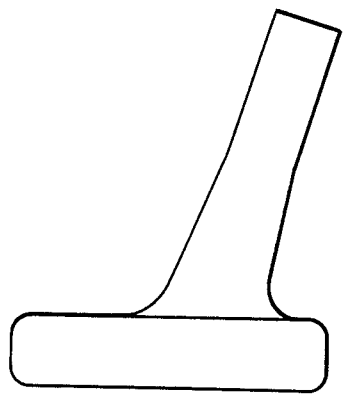
Figure 4B:
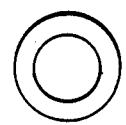

The angled stem (see FIGS. 4, 4a and 4b ) is specifically for the surgical situation where the malleus handle is further than 0.1 inch in the anterior to posterior dimension and when a laterally displaced promontory does not allow clearance under the malleus handle.

In all designs the stem of the implant is specifically designed to have a relatively broad stem within 0.0945 inches of the base then narrowing to 0.039 inches in diameter for the remaining distal portion of the stem. This narrow portion of the stem will allow the stem to reside on the stapes footplate or oval window graft membrane with sufficient clearance of the walls of the oval window niche to avoid contact which might impede vibratory motion of the implant. The broader diameter stem nearer the base allows greater cross-sectional area for creating a facet for the head of the stapes to provide further mechanical stability to the implant on the stapes.

Currently available materials for use in middle ear sound transformer reconstruction include autograft and homograft bone and cartilage, Plasti-Pore® Proplast® and Ceravital®. Autograft and homograft bone and cartilage require harvesting from human beings and in their natural shape are poorly designed for purposes of reconstruction and must be extensively machined prior to use. Plasti-pore® and Proplast® are porous materials, the first of which is hard polyethylene and the second a relatively soft felt-like material. Neither material lends itself to micro-contouring to fit individual patient needs. Both of these materials require cartilage to be interposed between the implant and the tympanic membrane (graft) to avoid extrusion. Ceravital® is an opaque bio-active ceramic which requires the use of bone pate between the implant surface and soft tissue of the tympanic membrane (graft) to achieve a bond. In addition, Ceravital® is more difficult to contour than is the bio-active glass ear prosthesis of the invention.

The positioning of the bio-active glass middle ear prostheses of the invention at reconstruction can be confirmed as they are transparent as are none of the other available prostheses and can be contoured as easily as bone to create an implant with features specific to the needs of the individual patient. The bio-active glass middle ear prosthesis of the invention can achieve stabilization within a reconstructed ossicular chain both through mechanical interlock provided by grooves and facets created at surgery into which other remaining parts of the ossicular chain are fitted and through bone and/or soft tissue bonding to remaining parts of the middle ear sound transformer system which may include any or all of the following tympanic membrane, tympanic membrane graft, malleus, incus, stapes superstructure, stapes footplate or oval window graft membrane.

All currently available middle ear prostheses have the general appearance of a tack or a stem and base but none combine the special characteristics of transparency, contourability and ability to bond to soft tissue and bone with design features with specific surgical reconstructive application as in the prostheses of the invention.

There are several advantages associated with the bio-active glass prostheses of the invention.

When the devices are constructed from bio-active glasses the implants bond by means of a soft tissue bond to the tympanic membrane and to the remaining components of the ossicular chain.

When the devices are made from bio-active glasses they have the advantage of ease of machining and ability to be contoured to meet the specification of the surgeon.

When the devices are made from bio-active glasses they are transparent and therefore can be used with an optical microscope to visualize relationship in the ossicular chain in which they will be placed, and ensure proper positioning and contact at the time of surgery.

We claim:

1. A middle ear prosthesis consisting essentially of a bio-active, bio-compatible glass comprising a substantially disc-like base member, one base surface of which is especially adapted to interface with and bond to the thin collagen layer of the tympanic membrane or grafted tympanic membrane of the middle ear and an integral substantially cylindrical stem member projecting outwardly form the other base surface of said base member, said stem member having a smaller diameter than said base member and the axis of said stem member being off-set with respect to the center of and substantially perpendicular to said base surface.

2. The middle ear prosthesis of claim 1 wherein the end of said stem member proximal to said base is flared.

* * * * *

UNITED STATES PATENT AND TRADEMARK OFFICE
CERTIFICATE OF CORRECTION

PATENT NO. : 4,676,796

DATED : June 30, 1987

INVENTOR(S) : Gerald E. Merwin; Derek B. Spilman; Larry L. Hench

It is certified that error appears in the above-identified patent and that said Letters Patent is hereby corrected as shown below:

Claim 1, line 8, change "form" to --from--.

Signed and Sealed this

Twenty-second Day of September, 1987

Attest:

DONALD J. QUIGG

*Attesting Officer*   *Commissioner of Patents and Trademarks*